United States Patent
Radley

(10) Patent No.: US 8,537,968 B2
(45) Date of Patent: *Sep. 17, 2013

(54) METHOD AND APPARATUS FOR INSPECTION OF MATERIALS

(75) Inventor: Ian Radley, Bishop Auckland Durham (GB)

(73) Assignee: Kromek Limited, Sedgefield Durham (GB)

( * ) Notice: Subject to any disclaimer, the term of this patent is extended or adjusted under 35 U.S.C. 154(b) by 231 days.

This patent is subject to a terminal disclaimer.

(21) Appl. No.: 12/989,035

(22) PCT Filed: Mar. 24, 2009

(86) PCT No.: PCT/GB2009/050270
§ 371 (c)(1),
(2), (4) Date: Jan. 7, 2011

(87) PCT Pub. No.: WO2009/130491
PCT Pub. Date: Oct. 29, 2009

(65) Prior Publication Data
US 2011/0116605 A1    May 19, 2011

(30) Foreign Application Priority Data
Apr. 24, 2008 (GB) ................... 0807473.4

(51) Int. Cl.
*G01N 23/06* (2006.01)

(52) U.S. Cl.
USPC ................... 378/53; 378/56; 378/62

(58) Field of Classification Search
USPC ................... 378/51, 53, 54, 56, 62
See application file for complete search history.

(56) References Cited

U.S. PATENT DOCUMENTS

| | | | |
|---|---|---|---|
| 3,818,232 A | 6/1974 | Kirkpatrick |
| 3,845,963 A | 11/1974 | Price |
| 5,493,596 A | 2/1996 | Annis |
| 6,246,747 B1 | 6/2001 | Wear et al. |

(Continued)

FOREIGN PATENT DOCUMENTS

| DE | 102005049586 | 4/2007 |
|---|---|---|
| WO | WO 2008/007976 | 1/2008 |

OTHER PUBLICATIONS

International Search Report and Written Opinion, dated Aug. 3, 2009, 13 pages.

(Continued)

*Primary Examiner* — Jurie Yun
(74) *Attorney, Agent, or Firm* — Drinker Biddle & Reath LLP

(57) ABSTRACT

A method of and apparatus for obtaining radiation transmission data and especially an image of an object in such manner that allows some data about relative proportions of constituent materials to be derived is described. A radiation source and a radiation detector system able to resolve transmitted intensity across a plurality of frequencies within the spectrum of the source are used to produce transmitted intensity data for each such frequency. Measured data is compared numerically to a mass attenuation data library storing mass attenuation data, individually or collectively, for a small number of expected constituent component materials to fit each intensity data item to the relationship given by the exponential attenuation law: $I/I_o = \exp[-(\mu/\rho)\rho t]$ in respect of the constituent component materials and derive therefrom an indication of relative proportions of each constituent component material. An image may be generated from the resolved transmitted intensity data.

22 Claims, 5 Drawing Sheets

(56) References Cited

U.S. PATENT DOCUMENTS

| | | |
|---|---|---|
| 7,369,642 B2 * | 5/2008 | Eilbert et al. .................. 378/57 |
| 8,233,588 B2 * | 7/2012 | Gibson et al. .................. 378/53 |
| 2006/0203956 A1 | 9/2006 | Raupach |
| 2007/0092056 A1 | 4/2007 | Flohr et al. |
| 2007/0144268 A1 | 6/2007 | Atkinson |
| 2007/0147584 A1 | 6/2007 | Hofman |
| 2011/0110493 A1 * | 5/2011 | Radley et al. .................. 378/83 |

OTHER PUBLICATIONS

USPTO Office Action dated Jul. 23, 2013, U.S. Appl. No. 12/988,978.

* cited by examiner

METHOD AND APPARATUS FOR INSPECTION OF MATERIALS

FIELD OF THE INVENTION

The invention relates to a method and apparatus for the inspection of materials. The invention relates especially to a method and apparatus that operates by or in conjunction with the generation of an image of the material, but is not limited to such imaging. The invention in particular relates to an apparatus and method making use of high energy radiation such as x-rays or gamma-rays to scan objects. The invention is especially suited to the determination of the relative proportions or relative extents of two or more component materials in a compound object where the identities of likely component materials are generally known, but where the precise proportions of those likely component materials represent an unknown in a given sample under inspection.

BACKGROUND

The principle of scanning objects with high energy radiation such as x-rays or gamma-rays, particularly to generate image information in the form of a transmission radiograph, is widely employed for example in the security industry, but might also be employed in other areas, for example, without limitation, medical imaging, imaging for quality control purposes or the purposes of determining the integrity of the structure, or the like.

Security scanning is particularly directed at the identification of undesirable materials or objects, and especially explosives or weapons, in airline baggage. Airport security must in particular ensure that no explosive material is allowed on board any aircraft. Various strategies are employed in order to achieve this goal. However one of the most important is the transmission screening of hold baggage using x-ray machines that have automated explosive detection capability. Radiation-based systems such as x-ray systems also find wide application in medical radiography and in some quality and process control applications.

Analysis based on transmitted radiation, whether for transmission radiography or otherwise, relies on the same general principle. The thicker or more dense an object is then the more it will be likely to attenuate an incident beam. By use of suitable detectors and a suitable source, transmitted intensity data can be used to derive information, for example in the form of radiographs, of an item under screening based on the absorption of an object or set of objects can be generated. X-Ray absorption has also been used for some time as the basis for screening objects to create some form of representational image of the contents or components thereof relative to each other in three-dimensional space.

This approach may be limited in that it tends to give limited information about the material content. At its simplest, all that is being measured is transmissivity. The detector merely collects amplitude information.

However, it is known that the absorption properties of any material can vary with energy, and that the amount by which the absorption properties vary depends in particular on atomic number. This has led to development of dual-band or dual-energy detectors which are capable of separately differentiating, at least to some degree, between low- and high-energy bands from the full spectrum of an x-ray source. U.S. Pat. No. 4,247,774 represents a general reference to the use of a dual-energy detector system in relation to computer assisted topography in a medical, imaging application.

A dual energy system confers only limited information about composition. Recent development of detectors that can resolve spectroscopic information about transmitted x-rays more effectively has led to the development of apparatus that discriminate across a larger range of bands and generate a larger plurality of images across these bands to generate multispectral images. For example U.S. Pat. No. 5,943,388 describes a system that makes use of cadmium telluride detectors to image across at least three energy bands and generate at least three images.

A particular problem presented by practical objects is that a practical object is rarely homogeneous, but is often composed of a number of constituent components each of which can be expected to have its own characteristic absorption properties. A conventional transmission radiograph, for example built up of data in one or two dimensions in an x, y plane generally perpendicular to a radiation beam direction is thus limited in that since it delivers information about transmitted intensity only it is only possible to show the cumulative absorption effect in the ray path in such a radiograph. To distinguish between such component materials, and to obtain an indication of the relative contribution of, and for example the relative thickness of, such component materials it has traditionally been necessary to employ more complex scanning geometries, for example so as to generate multiple ray paths through an object in multiple directions.

SUMMARY OF THE INVENTION

The invention is directed at the provision of a method and apparatus for scanning of objects that mitigates one or more of the above disadvantages of prior art scanning systems and methods.

In particular, the invention is directed at the provision of a method and apparatus for scanning of objects, and especially of objects comprising multiple component materials where the identities of likely component materials are generally known but where the precise proportions of those likely component materials represent an unknown in a given sample under inspection, to allow information about the relative proportions and/or extents of each component, especially in a transmitted beam direction, to be determined.

Therefore, according to one aspect of the invention there is provided a method of obtaining radiation transmission data from, and preferably an image of, an object comprising the steps of:

providing a radiation source and a radiation detector system spaced therefrom to define a scanning zone therebetween, the detector system being capable of detecting and collecting spectroscopically resolvable information about incident radiation;

collecting one or more datasets of intensity information about radiation incident at the detector system and hence transmissivity of an object in the scanning zone at at least one scanning position, from radiation transmitted through the object and received at the detector system;

resolving each said intensity dataset across a plurality of frequencies or frequency bands within the spectrum of the source to produce an intensity data item for each frequency/band;

comparing the intensity data items numerically to a mass attenuation data library storing mass attenuation data for a plurality of expected constituent component materials of the object in the scanning zone to fit each intensity data item to the relationship given by the exponential attenuation law:

$$I/I_0 = \exp[-(\mu/\rho)\rho t]$$

in respect of the said constituent component materials and deriving therefrom an indication of relative proportions of each component material in a transmission path producing the said intensity data items.

Preferably the step of comparing the intensity data items comprises deriving an overall mass attenuation coefficient for each intensity data item at its particular frequency and fitting the dataset of such calculated mass attenuation coefficients to data from the library and for example carrying out the steps of:

deriving an overall mass attenuation coefficient for an intensity data item at its particular frequency;

reading a mass attenuation coefficient for each such component material at the said frequency;

repeating for a plurality of data items at a sufficient number of frequencies that a single unique solution can be derived for the relative proportions of each component necessary to produce the said intensity data items.

The measured data is thus fitted numerically and for example iteratively to the stored library data until and over sufficient different frequencies that a relative proportion solution is derived.

However, other alternative numerical methods for storing and processing mass attenuation data, individually or collectively, for a plurality of expected component materials will readily suggest themselves. For example a database may contain information on the overall mass attenuation coefficients of a range of samples consisting of different ratios of the individual component materials. It would then be possible to look for the best match between the sample under test and the database and derive a relative proportion solution accordingly.

If the thickness of an object is known or can be measured prior to performing the numerical analysis the step of comparing the intensity data items numerically may comprise deriving from the calculated relative proportions of each component and a known object thickness the relative cumulative depths of each component in a transmission path direction. The radiation source preferably comprises a source to deliver high-energy radiation such as ionizing radiation, for example high energy electromagnetic radiation such as x-rays and/or gamma rays, or subatomic particle radiation, and the detection system is adapted correspondingly to detect radiation in this spectrum. The radiation source for example is a broadband x-ray or gamma-ray source capable of producing broad spectrum emission over a wide range of x-ray or gamma-ray energies. Such a source will be familiar, and is widely used. The detector system is adapted to generate spectroscopic information about the transmitted radiation. That is, the detector exhibits a spectroscopically variable response across at least a part and preferably a substantial part of the spectrum of the radiation source allowing spectroscopic information to be retrieved.

The transmission of such radiation through a material can be given by the exponential attenuation law, as follows:

$$I/I_0 = \exp[(-\mu/\rho)\rho t]$$

Where $\mu/\rho$=Mass attenuation coefficient, a material constant which is characteristic of the weighted elemental composition of a material I=Final intensity $I_0$=Initial intensity $\rho$=density of the material t=thickness of the material For each scanning event, a plurality of resolved intensity data item measurements, are obtained numerically, to provide representative information which can be correlated to the mass attenuation coefficient necessary to produce such an intensity pattern. As is described in greater detail below, most of the variables associated with a given scanning event are constant with respect to the frequency/energy of the incident radiation from the source. However, the mass attenuation coefficient varies with energy in characteristic way. Thus, inferences relating to the specific mass attenuation coefficient applicable to the transmission path through material under test for a given scanning event can be drawn for each intensity data item (i.e. at each frequency band).

A comparison is then made to a suitable database library of data representative of the mass attenuation coefficient for different component materials to give a more representative indication of what is being scanned.

The key to methodology of the invention lies in the realisation that in many instances the general identity of an object under test, and its general composition in the sense of its major likely constituent component materials, are both known. What is not known is the precise proportion of those major component materials.

In accordance with the invention, for a given target object under test, a relatively small number of major component materials are identified, at least in general terms, which together can be expected to constitute essentially the whole object in practice, save for the most minor constituents, and thus can be expected collectively to contribute essentially to the entire transmission response of the object during transmission testing. A mass attenuation coefficient data library stores mass attenuation coefficients representative of each of these component materials.

It should be understood that where used herein the term "component material" may refer to a single identifiable chemical species, or to a composite material made up of a number of individual material elements to be collectively identified, provided that such a composite material can be separately identified by development of general mass attenuation coefficient data characteristic of the composite as a whole for storage in the data library, in the manner of the invention. For example, in the case of organic liquids it might be desirable to determine for a liquid, such as milk, data for overall fat content, overall protein content, overall sugar content or the like, using stored library data for the generalised mass attenuation behaviour of milk fats, milk proteins, milk sugar, or milk solids in the generality. For example in the case of an object where one of the known or likely component materials is a composite solid in which the relative proportion of the two constituent materials in the composite are generally, it should in principle be possible to derive a characteristic mass attenuation coefficient for the composite and/or for the components as the application requires.

The key to the invention is that the majority of the parameters in the attenuation equation set out above are known, either to the extent that is necessary for the materials to be distinguished, from the data library of mass attenuation coefficients, or from measurement, or are constant for a given source and are therefore constant as between each intensity data item at a different frequency for a given scanning event. In particular, an object thickness is a constant which can be eliminated by performing calculations at multiple frequencies, and in a particularly preferred embodiment is known for example by measurement of the object prior to performance of the scan.

Thus, in the given relationship, an overall and spectrally resolved overall $I_0$ is known for the source, an overall sample thickness t is either known or can be normalised out as a constant, a value of $\mu/\rho$ is stored for each likely component material, and a spectrally resolved overall I is derived at a plurality of frequencies or frequency bands.

In this way, a scan can be performed where the only underlying variable is the overall mass attenuation coefficient. This can be determined from I and $I_0$. At a single frequency, all that can be determined is this overall mass attenuation coefficient for the sample. However, the invention is applicable to situations where the presence only of a small number of identified likely component materials can be presumed, each exhibiting its own characteristic functional variation of mass attenuation coefficient with radiation frequency. The contribution of each component material can be given by its effective contribution to the total attenuation which can be related directly by numerical analysis to its proportion by volume in the overall composition. The unknown can be rendered as the relative proportion of each contribution, and hence the relative proportion of each component material. By taking measurements at sufficient different frequency bands and performing a suitable iterative comparative process in the calculation means, this unknown can be eliminated and the plurality of measured intensity data items can be fitted to the single component material ratio capable of producing the observed relationship.

Data is resolved spectroscopically over a sufficient plurality of frequencies or frequency bands to derive such a unique component material ratio. Where only two potential component materials are present, spectral resolution into two bands only may be sufficient in theory, although more complete spectral resolution is always likely to be preferred. Where there are more component materials it will be necessary to resolve the spectrum more completely before a unique ratio can be correlated to the plurality of data items. Nevertheless, in accordance with the invention, provided a relatively small number of likely component materials can be identified for the target sample under test, a correspondingly relatively small number of intensity data items can be used to derive useful information about the ratio between those component materials.

Conveniently, the thickness of an object is known or measurable. In that case, a simple calculation allows derivation from ratio data of overall thickness data in the transmission path for each component. That is, the step of comparing the intensity data items numerically conveniently comprises deriving from the calculated relative proportions of each component and a known object thickness the relative cumulative depths of each component in a transmission path direction.

Of course, it will be appreciated that such a calculation can derive only general rendering of depth information in the radiation transmission direction. It does not, in and of itself, give any information about the specific geometry of any particular component structures. Nevertheless, by giving even this limited information in the transmission direction from a presumption that the overall transmitted signal can be analytically and iteratively fitted to a single unique solution representing the relative proportions of a relatively small number of known component materials in the transmission path, at least some information in the third dimension is obtained which can only be obtained in the prior art by much more complex geometrical arrangements, using multiple ray paths and the like.

The detector system is adapted to generate spectroscopic information about the transmitted radiation at a plurality of discrete energies and/or energy bands. Preferably, the detector exhibits a spectroscopically variable response across at least a substantial part of the spectrum of the radiation source allowing detailed spectroscopic information to be retrieved.

The resolved bandwidth is not directly pertinent to the invention and useful results can be obtained by any suitable approach to dividing the spectrum, either in whole or in part, into separate bands. For example, the entire spectrum or a substantial part thereof may simply be divided between such a plurality of bandwidths, and each data item be considered as a measure representative of intensity across the entire band, and for example an average intensity. Alternatively, a plurality of relatively wide bands, but with discrete gaps therebetween, may be envisaged and analysed on the same basis. Alternatively, "bands" may be narrow even to the point where they essentially approximate to an evaluation of intensity at a single energy. As used herein the concept of intensity at an energy "band" includes evaluation of intensity at such a discrete single energy as well as evaluation of intensity at an energy across a narrow or broad bandwidth. Nevertheless, it is generally preferable that imaging bands are relatively broad and that characteristic bands are relatively narrow.

Similarly the source may be a single broad spectrum source across which a plurality of bandwidths or single energies may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source may comprise an x-ray source having a relatively lower energy spectrum, for example operating below 60 keV and for example at 10 to 50 keV and one or more other sources such as radioisotope sources generating radiation at higher energies, for example above 100 keV.

If we consider the exponential attenuation equation, it can be seen that the mass attenuation coefficient is one of the terms listed. The mass attenuation coefficient itself is however dependent on the energy of the detected x-rays. The other terms in the equation have no dependence on the x-ray energy. Thus if one measures transmission at multiple energies it is possible to relate the variation in transmission functionally to the mass attenuation coefficient.

As this term is characteristic of each material present it is therefore possible in principle given sufficient data items to derive the relative contributions of each ingredient in a particular target liquid by fitting each variation to the dataset of total transmitted intensities (and to a dataset of total calculated mass attenuation coefficients at each energy, ie for each intensity data item) to derive a ratio of ingredients that uniquely fits the measured transmitted intensity dataset and the dataset of total calculated mass attenuation coefficients.

At its most basic, the invention allows identification of materials from collected and resolved transmission data based on a numerical analysis that provides, with reference to a suitable data library of equivalent or otherwise comparable data for a range of materials and/or components of objects likely to be encountered in a given application, an indication of relative material content. The data library may comprise information in any suitable form which can be related in a numerically analytical manner to data collected across the resolved energy bands in accordance with the invention. The data library may include standard preset reference materials and/or user input reference materials and/or reference data may be generated from known materials in accordance with the foregoing method. That is, a library of data may be built up by the system, which can in effect "learn" material characteristics, over time. The data library may comprise electronically stored data and/or data stored on a hard medium, such as a printed resource, and may be held and accessed locally and/or remotely, manually and/or automatically, none of which is directly pertinent to the operation of the method of the invention.

Thus, at its simplest, the invention in the first aspect may simply comprise a method for extracting from energy-related transmission data an indication of the mass attenuation coefficient, and therefore an indication of materials in the transmission path. It need not generate an image. No particular transmission beam geometry is mandated. A simple, effectively one-dimensional beam geometry incident upon a simple, single detector may be sufficient.

However, for practical purposes it may be preferable that the invention forms part of and supplements the information offered by a radiographic imaging system. In accordance with this embodiment, the dataset of information about radiation incidence collected at the detector is used to generate an image of an object in the scanning zone.

The data in the transmission beam direction resolved numerically by the method above may be used to supplement such an image.

For example the dataset of information about radiation incidence collected at the detector may be used to generate both a two dimensional image of an object in an x, y plane and comparative information regarding the relative proportions of each component material in a z direction corresponding to a transmission path.

More preferably the step of comparing the intensity data items numerically comprises deriving numerically from the calculated relative proportions of each component and from a known (for example previously or simultaneously measured) object thickness (ie path distance) the relative cumulative depths of each component in a z direction and the method further comprises presenting this numerically analysed supplementary cumulative depth information in the z direction for example to give a measure of volume rendering to the data and/or comprises representing this information in an image representation in the z direction.

Thus, in accordance with the methodology, a simple beam geometry which inherently in itself only produces a transmission radiograph in an x, y plane can also be used to generate some information in a third dimension. This can be done without complex beam geometries and multiple ray paths by the realisation that some information can be rendered in this direction by making use of spectral resolution of the transmitted x-rays, and by making use of knowledge of the object as comprising a limited number of potential component materials.

It must be appreciated that any "image" representation in the third dimension is necessarily a pseudo image only. The method of the invention, in and of itself, does not give full imaging capability in a third dimension from a two dimensional radiograph. In principle, all that can be derived, from a known overall thickness and a known relative proportion, is a rendering of overall thickness in the ray path for each component. Any image in the third dimension created therefrom is necessarily a modelled image only.

Nevertheless, particularly in instances where the underlying likely structure of an object, as well as its likely component materials, is reasonably known and predictable, a useful representative image in the third dimension might well be generated. For example, an image representation may be generated in a preferred embodiment of the method by deriving in accordance with the method a measure of relative thicknesses of each component material, making reference to a stored representative model of the approximate proportion and structure expected for each component material for an object of the class under test, and fitting the calculated relative proportions to the model in generating an image representation in the z direction.

Such an image representation might still generate usable information in the third dimension. For example, in some medical imaging applications, the general structure being imaged will be known. In those circumstances, while a representative image generated in accordance with the foregoing might not have the fundamental accuracy of a full CT scan or other 3D imaging method, it may still present the information in a way which assists in interpretation of the third dimension.

Optionally, information is collected regarding the transmissivity of an object in the scanning zone as the object is caused to move relative to and through the scanning zone to collect a plurality of datasets, which are conveniently used to generate a succession of images as an object moves through the scanning zone.

For clarification it should be understood that where used herein a reference to the generation of image is a reference to the creation of an information dataset, for example in the form of a suitable stored and manipulatable data file, from which a visual representation of the underlying structure of the object under investigation could be produced, and references to displaying this image are references to presenting an image generated from such a dataset in a visually accessible form, for example on a suitable display means.

The method of the invention conveniently further provides the additional step of displaying such generated image or images, and in the case of multiple images might involve displaying such images simultaneously or sequentially.

An essential requirement for implementation of the invention is that the detector system can generate spectroscopic information about the transmitted radiation. That is, the detector exhibits a spectroscopically variable response across at least a substantial part of the radiation spectrum of the source allowing spectroscopic information to be retrieved. A numerical analysis as above described is performed to obtain information representative of the proportional material content in a transmission path.

In the preferred embodiment, where an image is also generated, proper resolution of spectroscopic information confers a further advantage. It offers the potential by imaging across a series of bands to create several images which to some extent can reflect the different responses of materials and thus, by distinguishing between each image across each imaging band, for example by representing them differently (such as in different colours) in a resultant combined image, it assists in resolution of different objects, components or parts of the image.

Thus in accordance with a preferred embodiment of the invention, each collected image is resolved spectroscopically across a plurality of conveniently relatively broad "imaging" bands each intended to generate an image across a part of the overall spectrum, so that the imaging bands together allow the generation of an energy-differentiated composite image or succession of images in familiar manner. The number of imaging frequency bands is conveniently between 2 and 10, and for example between 4 and 8.

Spectroscopic detectors can then be operated in an energy selective manner, giving rise to the ability to present an image resolved into a significantly increased number of "imaging" energy bands compared with the two that are available from standard prior art dual energy detectors. This information can be used to improve resolvability of objects of different composition.

This is achieved in accordance with this preferred embodiment in that spectroscopic resolution of transmitted radiation in each such relatively broad band is represented in the generated image. For example, spectroscopic differentiation in the collected data is represented in the image as differentiated colour, shading or marking. A banded mapping is used in that the source spectrum is divided into a plurality of bands, for example between four and eight bands, and different colours are used to represent each such band in the displayed image. The apparatus conveniently includes suitable image processing means to effect this mapping.

An image or composite image or succession of images so generated is preferably displayed on a suitable display means such as a visual display screen.

By analogy to the above, in accordance with a further aspect of the invention there is provided an apparatus for scanning of and obtaining radiation transmission data from, and preferably an image of, an object comprising:

a radiation source and a radiation detector system spaced therefrom to define a scanning zone therebetween and to collect in use a dataset of information about radiation incident at the detector system and hence transmissivity of an object in the scanning zone at at least one scanning position;

a data processing apparatus to process and resolve each such dataset or image spectroscopically across a plurality of frequencies within the spectrum of the source to produce intensity data item for each frequency;

a mass attenuation data library storing mass attenuation data for f a plurality of expected constituent component materials of an object under test;

a comparator to fit each intensity data item to the relationship given by the exponential attenuation law:

$$I/I_0 = \exp[-(\mu/\rho)\rho t]$$

in respect of the constituent component materials and derive therefrom an indication of relative proportions of each constituent component material in a transmission path producing the said intensity data items.

Preferably, the comparator comprises a calculation means adapted to derive and fit to the data in the data library an overall mass attenuation coefficient for each intensity data item, for example in that it is adapted to: derive an intensity data item at its respective frequency; read an ingredient mass attenuation coefficient for each such ingredient at the said frequency; repeat at sufficient frequencies that a single unique solution can be derived to fit the relative proportions of each constituent ingredient to the said intensity data items.

However, the comparator may alternatively comprise calculation means adapted to derive and fit a data library to an overall mass attenuation coefficient for each intensity data item according to other alternative numerical methods for storing and processing mass attenuation data, individually or collectively. For example a data library may contain information on the overall mass attenuation coefficients of a range of samples consisting of different ratios of the individual component materials; the calculation means being adapted to derive the best match between the sample under test and the data library and derive a relative proportion solution accordingly.

Preferably the comparator is adapted to derive from the calculated relative proportions of each component and a known object thickness the relative cumulative depths of each component in a transmission path direction.

Conveniently, the apparatus comprises a means for prior measurement of the thickness of an object under test, determining a transmission path direction. For example, the apparatus includes a laser distance measurement means such as a laser interferometer.

The apparatus of the invention has a comparator that effects a comparison between the stored data in the data library and the derived data from the scan, and in particular includes calculation means at least to calculate a mass attenuation coefficient for each intensity data item and compare and fit the same to the library data. Any suitable form of comparator combining suitable hardware and software, and for example a suitably programmed data processing apparatus such as a suitably programmed general purpose or special purpose computer, can be envisaged.

It will be understood generally that each numerical step in the method of the invention can be implemented by a suitable set of machine readable instructions or code. These machine readable instructions may be loaded onto a general purpose computer, special purpose computer, or other programmable data processing apparatus to produce a means for implementing the functions specified, and in particular to produce a comparator or calculation means as herein described.

These machine readable instructions may also be stored in a computer readable medium that can direct a computer or other programmable data processing apparatus to function in a particular manner, such that the instructions stored in a computer readable medium produce an article of manufacture including instruction means to implement some or all of the steps in the method of the invention. Computer program instructions may also be loaded onto a computer or other programmable apparatus to produce a machine capable of implementing a computer executed process such that the instructions are executed on the computer or other programmable apparatus providing steps for implementing some or all of the steps in the method of the invention. It will be understood that a step can be implemented by, and a means of the apparatus for performing such a step composed in, any suitable combinations of special purpose hardware and/or computer instructions.

Optionally, the apparatus is adapted to collect in use transmission intensity data with an object in a single scanning position and for example includes a means to retain an object in a scanning position such as a receptacle into which an object can be placed. Additionally or alternatively it may include a conveyor to convey an object into and out of such scanning position.

Optionally, the apparatus is adapted to collect in use transmission intensity data with an object in a plurality of scanning positions as the object moves through the scanning zone, and preferably to collect in use data for an image of an object in the scanning zone, and preferably a succession of images as the object moves through the scanning zone, in that it further comprises an object handler to cause an object to move relative to and through the scanning zone in use.

Optionally, the apparatus further includes an image generation apparatus to generate at least a first image from the output of the detector system; and optionally further an image display adapted to display an image.

The image is conveniently a one or two dimensional transmission radiograph. Numerically analysed data from the comparator may supplement this image. For example the apparatus is adapted to use transmission intensity data to generate a one- or two-dimensional image of an object in an x, y plane generally perpendicular to an incident radiation transmission path and to use comparative numerically analysed information regarding the relative proportions of each component material data in a z direction corresponding to a transmission path to generate supplementary information in the z direction for example to give a measure of volume rendering to the data and/or the apparatus is adapted to use such information to generate an image representation in the z direction.

The display means is conveniently a simple two dimensional display screen, for example a conventional video display screen (which term is intended to encompass any direct display or projection system exploiting any cathode ray tube, plasma display, liquid crystal display, liquid crystal on silicon display, light emitting diode display or like technology). It is a particular advantage that the method can be envisaged for use with, and the apparatus for the invention incorporated into, the standard display screens of comparable existing systems for example in the security or medical imaging fields.

The radiation source must produce a distribution of energies across a suitable spectral range for characteristic scattering, and is typically an x-ray source. Tungsten is the most appropriate target, but others could be used.

The source may be a single broad spectrum source across which a plurality of bandwidths (which term, as described above, encompasses herein single energies) may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source comprises an x-ray source having a relatively lower energy spectrum, for example operating below 60 keV and for example at 10 to 50 keV and one or more radioisotope sources generating radiation at higher energies, for example above 100 keV.

A detector system in accordance with the invention may comprise a single detector or a plurality of discrete detector elements making up a multi-element system. In particular for non-imaging applications operating an effectively zero-dimensional intensity only analysis a single detector may be preferred. For imaging applications a linear or area array may be preferred.

It is necessary that the detector system is enabled to detect radiation in a manner which is spectroscopically resolvable. Preferably, a detector system, or some or all discrete detector elements making up a multi-element system, may be adapted to produce spectroscopic resolution in that it exhibits a direct spectroscopic response. In particular a system or element is fabricated from a material selected to exhibit inherently as a direct material property a direct variable electrical and for example photoelectric response to different parts of the spectrum. For example, the detector system or element comprises a wide direct bandgap semiconductor material. For example, the detector system or element comprises a semiconductor material or materials preferably formed as a bulk crystal, and for example as a bulk single crystal (where bulk crystal in this context indicates a thickness of at least 500 μm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_bTe$ where a and/or b may be zero.

Combination of these and any other such materials may be considered which give spectroscopic x-ray or other radiation detection rather than merely detecting amplitude of transmitted radiation and thus enable resolution at least of characteristic absences/amplitude reductions in the transmitted radiation indicating presence of a characteristic target species.

The image generation apparatus may be adapted to receive from the data processor a plurality of spectroscopically resolved images from a plurality of "imaging" bands and display these images successively or simultaneously to aid in object differentiation as above described. For example spectroscopic differentiation in the collected data is represented in a single combined image as differentiated colour, shading or marking.

A collimator is preferably provided to produce an emitted beam of suitable geometry from the radiation source. The geometry of the emitted beam will determine the most useful geometry of the detector system. At its simplest, particularly if the apparatus is being used purely to collect spectrally resolved transmission data for the purposes of deriving numerically an indication of mass attenuation coefficient, a simple, effectively one dimensional beam may be provided in conjunction with a simple single transmission detector.

However, in the preferred embodiment, the apparatus is further adapted for the generation of imaging information. It is intended in a possible mode of operation that the material identification provided in accordance with the numerical analysis method underlying the invention will serve in conjunction with imaging as an additional aid in the scanning of suspicious objects and in the identification of articles or materials therein, rather than being used in isolation. It is an advantage of the approach of the invention that useful compositional and imaging data can be obtained in principle for the same scan. More useful imaging data will generally be obtained by more complex beam and detector geometries, but the invention is applicable to all such geometries.

BRIEF DESCRIPTION OF THE DRAWINGS

The invention will now be described by way of example only with reference to the accompanying drawings in which.

DESCRIPTION OF THE PREFERRED EMBODIMENTS

Figure 1:
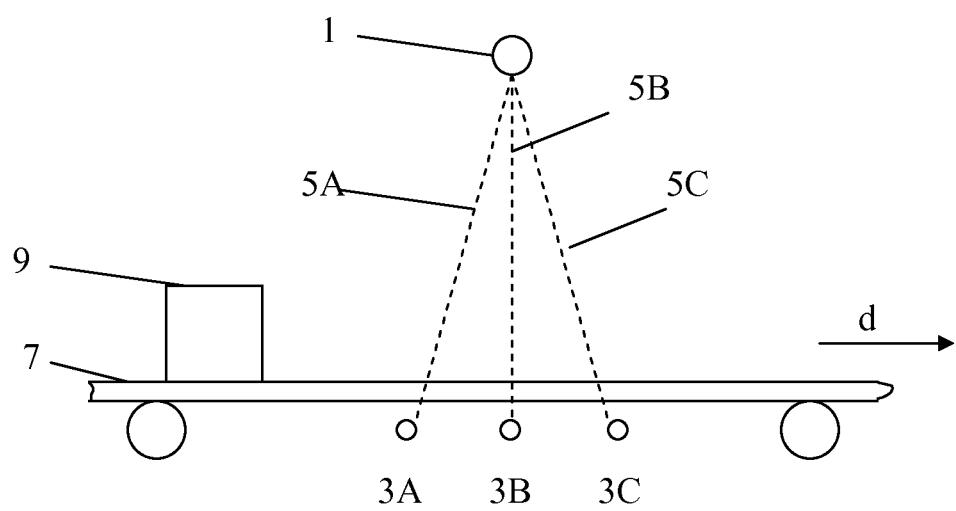
FIG. 1 is a side view of a representation of a scanning apparatus suitable for use in an embodiment of the invention.

Referring to FIG. 1, a suitable x-ray source 1 is used to direct x-rays via a scanning zone in the direction of three linear detectors 3a to 3c.

As has previously been discussed, an envisaged apparatus in accordance with the invention may combine the energy-resolved data collection and manipulation aspect of the invention to give a capability of determination of relative proportions and for example depths in a beam direction with the information provided by generating an image. A two-dimensional image gives information in an x, y plane generally perpendicular to a transmitted beam direction and the principles of the invention give some information, for example relative depth rendering, in a z-direction. The examples below all presume such a two-dimensional radiograph is generated. However it will be understood that the principles of the invention are equally applicable to non-imaging situations.

With this application in mind the illustrated embodiment uses a single x-ray source collimated to produce a curtain beam incident upon the three linear detectors 3a to 3c (which in the embodiment each comprise a linear array of detector elements). Thus, a plurality of ray paths 5a to 5c are generated in the scanning zone by means of a plurality of curtain beams incident upon a linearly or angularly spaced array of such linear detectors. Incident ray paths 5a to 5c are shown through the scanning zone between the x-ray source 1 and, respectively, the detectors 3a to 3c.

In the embodiment, the linear array detectors 3a to 3c comprise material capable of spectroscopic resolution of incident x-rays, and in the specific example comprise cadmium telluride although the skilled person will appreciate that other material selections may be appropriate. To exploit this spectral resolution, the x-ray source emits x-rays across a broad energy spectrum. In the example a tungsten source is used, although the skilled person would appreciate that other materials might be appropriate.

An endless belt conveyor 7 causes an object to be scanned 9 to move in a direction d so as to intercept the ray paths 5a to 5c in the scanning zone. The envisaged application of this embodiment of the invention is as a security scanner, and object 9 can be considered typically to be a container that is expected to contain a variety of distinct objects which it would be useful and desirable to characterise compositionally and to view effectively in a third dimension (for example, an item of airline hold baggage). However, the skilled person would readily appreciate that the same principles can be applied for example to the scanning of objects for internal examination purposes, to medical scanning, and to similar applications.

Figure 3:
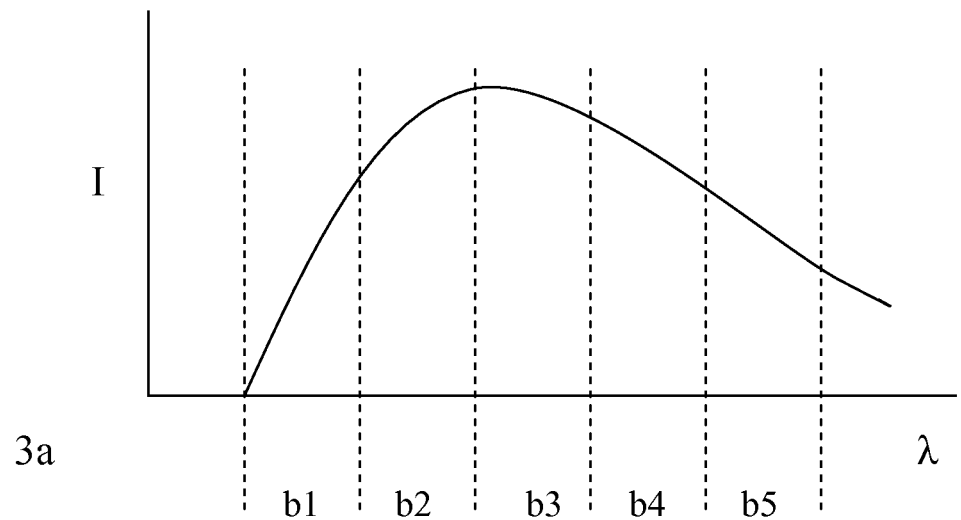
FIG. 3 illustrates a typical radiation source spectrum, and illustrates how it is partitioned to implement the invention in conjunction with an imaging operation.
Figure 3:
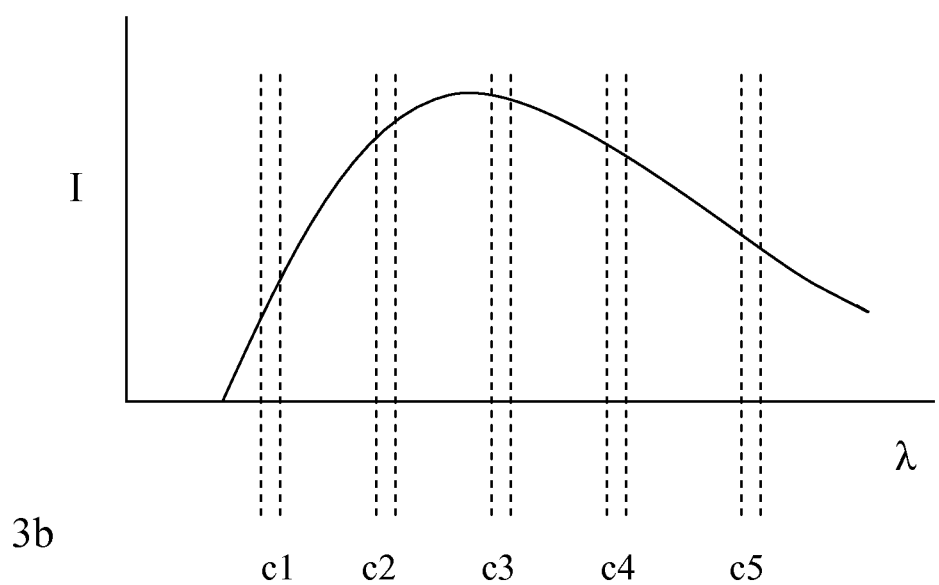
Figure 4:
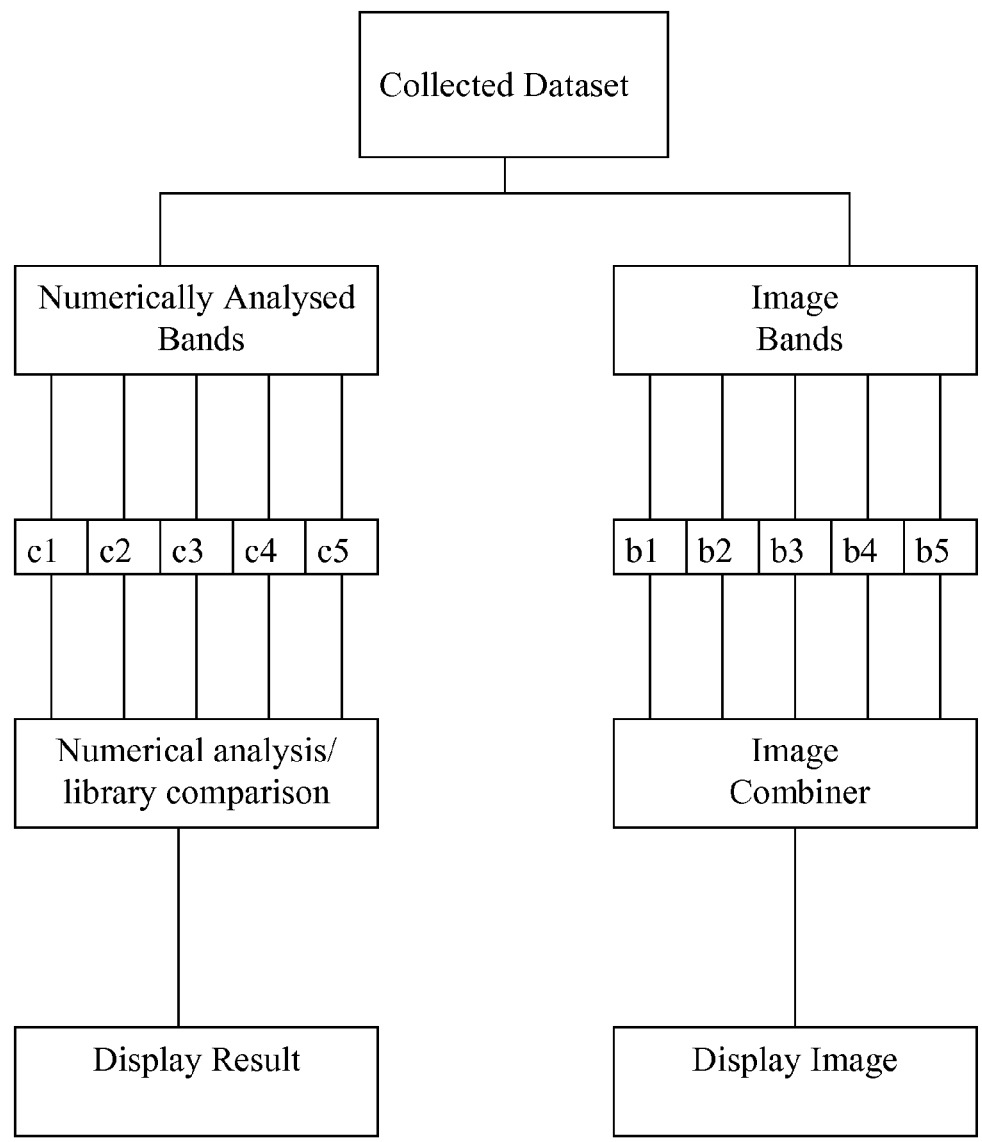
FIG. 4 is a schematic protocol for operation of the invention in conjunction with an imaging operation.

Datasets of transmitted intensity information are generated by building up transmitted information from each of the three detectors 3a to 3c. The processing of a dataset of information by resolving, at least to some extent, a relationship between incident energy/wavelength and transmitted intensity for both numerical analysis in accordance with the principles of the invention and spectroscopically resolved imaging purposes is illustrated in FIGS. 2 to 4.

Figure 2:
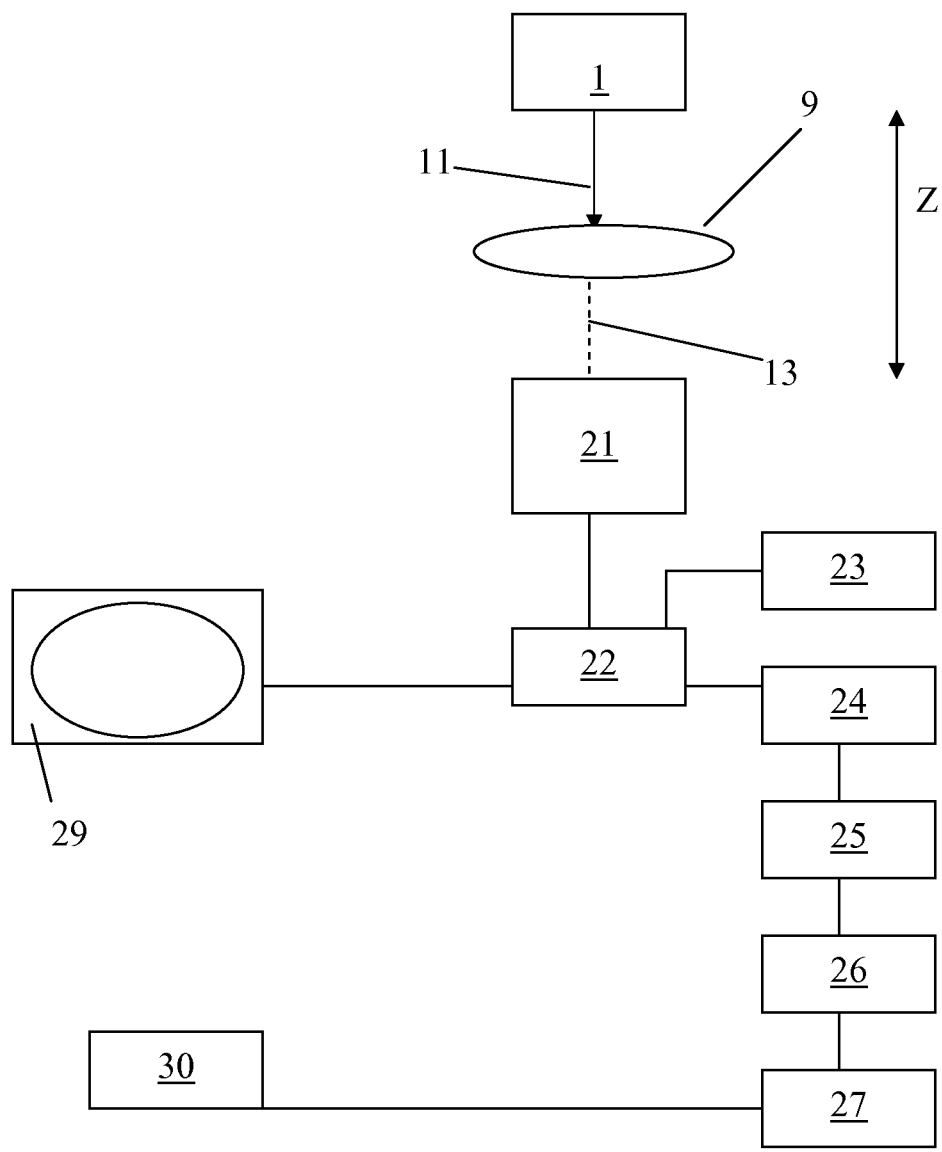
FIG. 2 is general schematic of a possible apparatus to implement the invention including a scanner of FIG. 1.

In the general schematic representation on FIG. 2, a single ray path only is shown for simplicity. An x-ray source 1 and laterally spaced detector apparatus assembly 21 together define a scanning zone Z between them. In use, an object to be scanned is brought into and through the scanning zone in the usual manner, for example on a suitable conveyor belt as above.

In the illustrated example, an object 9 sits in the scanning zone Z. An incident beam 11 from the x-ray source is illustrated. In this simple schematic, the incident beam is represented by the line 11. The transmitted beam 13 is incident upon a detector array 21.

The detector array 21 is in data communication with a processor 22. The detector array is used to generate a two dimensional "slice" in familiar manner. The inherent spectral resolution of the material in the array allows the processor 22 to resolve this image differentially across a plurality of pre-set frequency/energy bands in accordance with the principles of the invention by reference to energy band boundaries stored in the data register 23.

In the example embodiment a tungsten x-ray source, is used. A typical spectrum such as might be generated by tungsten of initial intensity against wavelength is illustrated in FIG. 3.

The main purpose of FIG. 3 is to illustrate two possible ways in which the spectrum may be resolved in accordance with the principles of the invention. In each case, the spectrum is resolved across five frequency bands.

The schematic illustrates two ways in which the spectrum may be resolved. In FIG. 3a, the bulk of the generated spectrum is divided between five relatively broad energy bands b1 to b5. In FIG. 3b, five relatively narrow bands, which may approximate even to individual energies, are defined c1 to c5. Neither alternative is in contradiction with the principles of the invention, and any combination may be used to generate useful results either for the numerical analysis of the invention or, in a preferred embodiment, for spectroscopically resolved imaging to give further information about an object under investigation.

In the preferred embodiment, the data is also used to generate an image, and most preferably a spectrally resolved image which is spectrally resolved itself across a plurality of frequency bands to give further information to the image. In such an embodiment, some of the resolved energy bands in FIG. 3, for example those illustrated in FIG. 3a, could be used to build up an energy-differentiated image for transmission to the display means 29. In this regard, the apparatus follows the same basic principles as conventional energy-differentiated imaging apparatus.

It differs in the functionality provided by the processor 22 which further acts in relation to a series of identified frequency bands, for example those in FIG. 3b, but in this function uses the data to generate a representative quantification of, and for example an average of, transmitted intensity in each band, which is then passed to the intensity data item register 24 for storage.

A calculation means 25 and comparator means 26 either or both for example comprising a suitably programmed data processor such as a special purpose or general purpose computer co-operably compare the data thereby produced with a library of data 27. The library of data includes pre-stored data of similar or at least numerically comparable nature which is related to or depends upon the mass attenuation coefficient for a small number of specified target component materials for a given object under test. Data may be preloaded or referenced, or may be generated or added to over time by operation of the apparatus with known materials.

Any of the data processing or storage elements of the apparatus, for example including one or more of the processor 22, data register 24, calculation means 25, comparator means 26 and data library 27, may be provided by a suitably programmed data processor means such as a special purpose or general purpose computer.

By virtue of this comparison, inferences may be drawn about the likely content in the transmission path and in particular about the likely proportions of the limited number of component materials. This is effected in that the calculation means 25 and comparator means 26 are co-operably adapted to perform an iterative calculation to fit the measured data to the library by deriving a weighting for the relative contribution of each component, and hence a measure of the proportional content. The mass attenuation equation which is applied is set out hereinabove. If the apparatus is used in accordance with the principles of the invention, it can be seen that all of the variables therein are either known from the source (which is of a fixed initial intensity and known spectrum) or normalized our or measurable (eg thickness). The mass attenuation coefficients of each ingredient likely to make any substantive contribution to the overall transmission intensity are also known. The overall transmitted intensity attenuation, and where t is known the specific mass attenuation coefficient, at a given frequency can be readily determined numerically by the calculation means 25 and comparator means 26 from the intensity data set. What is not known, at any single given frequency, is the contribution of each individual ingredient to that overall attenuation. However, the mass attenuation coefficient of each ingredient varies characteristically and differently with energy. Accordingly, it is at least possible in principle in accordance with the invention, by fitting the data for all the known mass attenuation coefficients for all the components to the calculated value at each energy, to derive a unique solution for the relative proportions of each component. This unique solution can be delivered to the display means 30, for example in association with the image display 29. In addition to its value in isolation, this may be used in conjunction with the image displayed on the display means 29 the better to characterise the contents or composition of an object under investigation.

In this way, in accordance with the invention, provided general knowledge of the likely constituents of an object under test is available, and data concerning these likely constituents can be stored, relative compositional information can be obtained. This may be used to supplement the two dimensional radiographic image with a representation of structure in the third direction.

For example, the library of data 27 may also store an approximate model structure for an object. Once the iterative calculation process described above has been performed to derive specific data about the relative proportions each component in the transmission path, and hence about their relative depth contributions to the total, a relative depth value for each component can be generated and fitted to the model in order to render a model image in the transmission direction. This can be used in conjunction with specific transmission radiography in the plane perpendicular to the transmission direction generated as above in conventional manner to give a degree of volume rendering of the data. Fundamentally, the data has specific transmission information only in two dimensions, but some degree of modelling in a third dimension is rendered possible in accordance with the invention by deriving the relative proportions of a relatively small number of expected or likely components using the spectral resolution of the apparatus.

The data collection and manipulation process is illustrated by the flow chart of FIG. 4, again for a preferred embodiment in which spectral resolution of transmitted intensity is used both for the numerical identification process of the invention and for an additional imaging purpose. Reading from top to bottom, the collected dataset is resolved both into the series of image bands and into the series of bands for numerical analysis in the manner illustrated in FIG. 3.

Resolution of a transmitted intensity dataset into image bands produces a series of images b1, b2, b3, b4 and b5 which together represent intensities of transmitted x-rays across relatively broad band widths but differentiated for energy for across the spectrum. In this way a degree of differentiation between objects of different composition is possible. Objects of different composition, and in particular a different atomic number, will tend to exhibit varying responses. If the different images b1 to b5 are for example successively displayed, or, more preferably, given distinctive colourations and displayed simultaneously in a single composite image, additional resolution of objects from the scan can be provided. This process is reasonably conventional.

Where the invention notably differs is in the additional resolution of the transmitted intensity dataset into bands c1 to c5. In the embodiment these bands are relatively narrow, but this is illustrative only. There is no reason in principle why the same bands could not be used for both purposes. The resolved transmission data for these bands in the register 25 are processed as above to generate intensity data and then a comparator references equivalent stored data to allow inferences to be drawn about proportional material content. This may be displayed for example in combination with the complex image generated from the imaging band resolution or as an additional information display in association with the image or on a bespoke display.

Figure 5A:
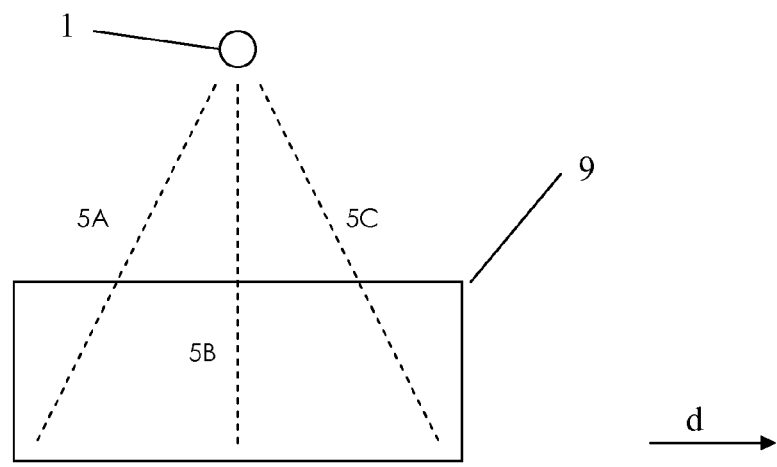
FIG. 5 illustrates the effect that can be created by images generated by means of the multiple ray paths provided by the embodiment of FIG. 1.
Figure 5B:
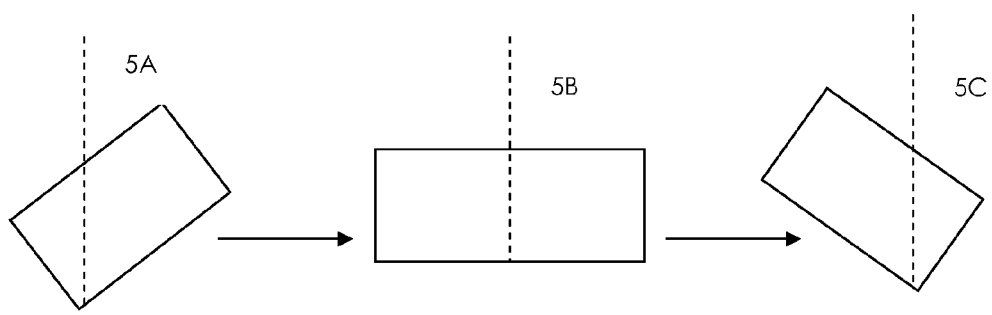

Although the invention, especially in non-imaging mode of operation, requires only a single ray path, the embodiment of FIG. 1 presented plural ray paths through an object. FIG. 5 illustrates an additional effect that can be created by images generated by means of the multiple ray paths provided by the embodiment of FIG. 1 which can further enhance the information provided. As an object 9 passes through incident ray paths 5a to 5c (see FIG. 5a) three images are generated in which the object is oriented differently relative to the x-ray source 1. Successive display of these images will cause the object to appear to rotate as is illustrated in FIG. 5b. This ability in effect to get a view of the object which is in effect rotatable in a third dimension can further enhance the image presentation.

The invention claimed is:

1. A method of obtaining radiation transmission data from an object comprising the steps of:
    providing a radiation source and a radiation detector system spaced therefrom to define a scanning zone therebetween, the detector system being capable of detecting and collecting spectroscopically resolvable information about incident radiation in that the detector system comprises at least one detector that exhibits a spectroscopically variable response allowing spectroscopic information to be retrieved;
    collecting one or more datasets of intensity information about radiation incident at the detector system and hence transmissivity of the object in the scanning zone at least one scanning position, from radiation transmitted through the object and received at the detector system;
    resolving each said intensity dataset across at least three frequencies or frequency bands within a spectrum of the source to produce an intensity data item for each frequency or frequency band;
    comparing the intensity data items numerically to a mass attenuation data library storing mass attenuation data for a plurality of expected constituent component materials of the object in the scanning zone to fit each intensity data item to a relationship given by the exponential attenuation law:

$$I/I_o = \exp[-(\mu/\rho)\rho t]$$

in respect of the constituent component materials and derive therefrom an indication of relative proportions of each component material in a transmission path producing the said intensity data items.

2. A method in accordance with claim 1 wherein the step of comparing the intensity data items comprises:
    deriving an overall mass attenuation coefficient for an intensity data item its frequency or frequency band;
    reading a mass attenuation coefficient for each such component material at the said frequency or frequency band;

repeating at sufficient frequencies that a single unique solution can be derived for the relative proportions of each component necessary to produce the said intensity data items.

3. A method in accordance with claim 1 wherein the step of comparing the intensity data items numerically comprises deriving from the calculated relative proportions of each component and a known object thickness the relative cumulative depths of each component in a transmission path direction.

4. A method in accordance with claim 1 wherein the dataset of information about radiation incidence collected at the detector is used to generate an image of the object in the scanning zone.

5. A method in accordance with claim 4 comprising the additional step of displaying the generated image or images.

6. A method in accordance with claim 5 wherein a succession of images is generated, and each such image is resolved spectroscopically across the plurality of frequencies or frequency bands within the spectrum of the source which are allocated to generate a series of energy-differentiated images.

7. A method in accordance with claim 1 wherein the dataset of information about radiation incidence collected at the detector is used to generate a two dimensional image of the object in an x, y plane and comparative information regarding the relative proportions of each component material in a z direction corresponding to the transmission path.

8. A method in accordance with claim 7 wherein the step of comparing the intensity data items numerically comprises deriving from the calculated relative proportions of each component and a known object thickness the relative cumulative depths of each component in the z direction and the method further comprises representing this information in an image representation in the z direction.

9. A method in accordance with claim 8 comprising deriving a measure of relative thicknesses of each component material, making reference to a stored representative model of the approximate proportion and structure expected for each component material for an object of the class under test, and fitting the calculated relative proportions to the model in generating the image representation in the z direction.

10. A method in accordance with claim 1 comprising the additional step of causing the object to move relative to and through the scanning zone and thereby collecting a plurality of successive datasets.

11. A method in accordance with claim 10 wherein the plurality of successive datasets are used to generate a corresponding plurality of successive images as the object moves relative to and through the scanning zone.

12. An apparatus for scanning of and obtaining radiation transmission data from an object comprising:
a radiation source and a radiation detector system spaced therefrom to define a scanning zone therebetween and to collect in use a dataset of information about radiation incident at the detector system and hence transmissivity of an object in the scanning zone at at least one scanning position, the radiation detector system being capable of generating spectroscopic information about the transmitted radiation in that the detector system comprises at least one detector that exhibits a spectroscopically variable response allowing spectroscopic information to be retrieved;
a data processing apparatus to process and resolve each such dataset or an image spectroscopically across at least three frequencies or frequency bands within a spectrum of the source to produce intensity data item for each frequency or frequency band;
a mass attenuation data library storing mass attenuation data for a plurality of expected constituent component materials of the object under test;
a comparator to fit each intensity data item to a relationship given by the exponential attenuation law:

$I/I_o = \exp[-(\mu/\rho)\rho t]$ in respect of the constituent component materials and derive therefrom an indication of relative proportions of each constituent component material in a transmission path producing the said intensity data items.

13. An apparatus in accordance with claim 12 wherein the comparator comprises a calculation means adapted to:
derive an overall mass attenuation coefficient for an intensity data item at its frequency or frequency band;
read a mass attenuation coefficient for each such constituent component material at the said frequency or frequency band;
repeat at sufficient frequencies that a single unique solution can be derived to fit the relative proportions of each constituent component material to the said intensity data items.

14. An apparatus in accordance with claim 12 wherein the comparator is adapted to derive from the calculated relative proportions of each component and a known object thickness the relative cumulative depths of each component in a transmission path direction.

15. An apparatus in accordance with claim 12 further comprising an object handler to cause the object to move relative to and through the scanning zone in use.

16. An apparatus in accordance with claim 12 further including an image generation apparatus adapted co-operably with the detector to collect in use data for at least one image of the object in the scanning zone and to generate at least one image from the output of the detector system.

17. An apparatus in accordance with claim 16 further including an image display means adapted to display at least one image.

18. An apparatus in accordance with claim 16 adapted to use transmission intensity data to generate a two dimensional image of the object in an x, y plane and to use comparative information regarding the relative proportions of each component material in a z direction corresponding to the transmission path to generate an image representation in the z direction.

19. An apparatus in accordance with claim 12 wherein a detector is adapted to produce spectroscopic resolution in that it is fabricated from a material selected to exhibit inherently as a direct material property a direct variable electrical response to different parts of the x-ray spectrum.

20. An apparatus in accordance with claim 19 wherein the detector comprises a semiconductor material selected from cadmium telluride, cadmium zinc telluride (CZT), cadmium manganese telluride (CMT), germanium, lanthanum bromide, or thorium bromide.

21. An apparatus in accordance with claim 19 wherein the detector comprises a semiconductor material or materials formed as bulk crystal including a Group II-VI semiconductor material.

22. An apparatus in accordance with claim 21 wherein the detector comprises a semiconductor material selected from cadmium telluride, cadmium zinc telluride (CZT), or cadmium manganese telluride (CMT).

* * * * *

UNITED STATES PATENT AND TRADEMARK OFFICE
CERTIFICATE OF CORRECTION

PATENT NO.        : 8,537,968 B2                                        Page 1 of 1
APPLICATION NO. : 12/989035
DATED             : September 17, 2013
INVENTOR(S)       : Ian Radley It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 326 days.

Signed and Sealed this

Fifteenth Day of September, 2015

Michelle K. Lee
*Director of the United States Patent and Trademark Office*